US011912923B2

(12) United States Patent
Rao et al.

(10) Patent No.: US 11,912,923 B2
(45) Date of Patent: *Feb. 27, 2024

(54) 1,2,3,3,3-PENTAFLUROPROPENE PRODUCTION PROCESSES

(71) Applicant: THE CHEMOURS COMPANY FC, LLC, Wilmington, DE (US)

(72) Inventors: Velliyur Nott Mallikarjuna Rao, Wilmington, DE (US); Mario Joseph Nappa, Leesburg, FL (US); Allen Capron Sievert, Elkton, MD (US)

(73) Assignee: THE CHEMOURS COMPANY FC, LLC, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/206,127

(22) Filed: Jun. 6, 2023

(65) Prior Publication Data

US 2023/0313012 A1 Oct. 5, 2023

Related U.S. Application Data

(60) Continuation of application No. 17/336,575, filed on Jun. 2, 2021, now Pat. No. 11,708,516, which is a continuation of application No. 16/458,350, filed on Jul. 1, 2019, now Pat. No. 11,053,421, which is a continuation of application No. 14/050,636, filed on Oct. 10, 2013, now Pat. No. 10,392,545, which is a division of application No. 13/539,963, filed on Jul. 2, 2012, now abandoned, which is a division of application No. 12/301,065, filed as application No. PCT/US2007/014646 on Jun. 22, 2007, now Pat. No. 8,263,816.

(60) Provisional application No. 60/816,649, filed on Jun. 27, 2006.

(51) Int. Cl.
| | |
|---|---|
| *C09K 5/04* | (2006.01) |
| *C07C 17/00* | (2006.01) |
| *C07C 17/087* | (2006.01) |
| *C07C 17/20* | (2006.01) |
| *C07C 17/23* | (2006.01) |
| *C07C 17/354* | (2006.01) |
| *C07C 19/08* | (2006.01) |
| *C07C 19/10* | (2006.01) |

(52) U.S. Cl.
CPC ............ *C09K 5/045* (2013.01); *C07C 17/00* (2013.01); *C07C 17/087* (2013.01); *C07C 17/206* (2013.01); *C07C 17/23* (2013.01); *C07C 17/354* (2013.01); *C07C 19/08* (2013.01); *C07C 19/10* (2013.01)

(58) Field of Classification Search
CPC ........ C09K 5/045; C09K 9/044; C07C 17/00; C07C 17/087; C07C 17/206; C07C 17/23; C07C 17/354; C07C 19/08; C07C 19/10

USPC ........................................................ 252/67
See application file for complete search history.

(56) References Cited

U.S. PATENT DOCUMENTS

| | | | |
|---|---|---|---|
| 2,437,993 | A | 3/1948 | Benning et al. |
| 2,466,189 | A | 4/1949 | Waalkes |
| 4,873,381 | A | 10/1989 | Kellner et al. |
| 5,136,113 | A | 8/1992 | Rao |
| 5,326,914 | A | 7/1994 | Baker |
| 5,396,000 | A | 3/1995 | Nappa et al. |
| 5,523,501 | A | 6/1996 | Kellner et al. |
| 5,679,875 | A | 10/1997 | Aoyama et al. |
| 5,716,590 | A | 2/1998 | Roewer et al. |
| 5,856,593 | A | 1/1999 | Powell et al. |
| 6,031,141 | A | 2/2000 | Mallikarjuna et al. |
| 6,294,055 | B2 | 9/2001 | Herkelmann et al. |
| 6,540,933 | B1 | 4/2003 | Sievert et al. |
| 7,189,884 | B2 | 3/2007 | Mukhopadhyay et al. |
| 7,230,146 | B2 | 6/2007 | Merkel et al. |
| 7,279,451 | B2 | 10/2007 | Singh et al. |
| 7,285,692 | B2 | 10/2007 | Rao et al. |
| 7,345,209 | B2 | 3/2008 | Mukhopadhyay et al. |
| 7,659,435 | B2 | 2/2010 | Rao et al. |
| 7,678,949 | B2 | 3/2010 | Rao et al. |
| 8,017,817 | B2 | 9/2011 | Rao et al. |

(Continued)

FOREIGN PATENT DOCUMENTS

| | | |
|---|---|---|
| DE | 1237084 B | 3/1967 |
| EP | 0644173 A1 | 3/1995 |

(Continued)

OTHER PUBLICATIONS

Null, Harold, Phase Equilibrium in Process Design, Wiley-Interscience Publisher, 1970, pp. 124 to 126.
Paleta et al., Synthesis of Perfluoroallylchloride and Some Chlorofluoropropenes, Bulletin de la Societe Chimique de France, Societe Francaise De Chimie, 1986, pp. 920-924.
R. N. Haszeldine et al., The Addition of Free Radicals to Unsaturated Systems. Part III, Chlorotrifluoroethylene, J. Chem. Soc., 1953, pp. 1592-1600.
Reid, Prausnitz and Poling, The Properties of Gases and Liquids, Chapter 8, pp. 241 to 387, 4th Edition, publisher McGraw Hill.
Satterfield, Charles N., Catalyst Preparation and Manufacture, Heterogenous Catalysis in Industrial Practice, 1991, pp. 87 to 112 2nd edition (McGraw-Hill, New York.

(Continued)

*Primary Examiner* — Douglas J Mc Ginty

(57) ABSTRACT

A process is disclosed for making $CF_3CF=CHF$. The process involves reacting $CF_3CClFCCl_2F$ with $H_2$ in a reaction zone in the presence of a catalyst to produce a product mixture comprising $CF_3CF=CHF$. The catalyst has a catalytically effective amount of palladium supported on a support selected from the group consisting of alumina, fluorided alumina, aluminum fluoride and mixtures thereof and the mole ratio of $H_2$ to $CF_3CClFCCl_2F$ fed to the reaction zone is between about 1:1 and about 5:1. Also disclosed are azeotropic compositions of $CF_3CClFCCl_2F$ and HF and azeotropic composition of $CF_3CHFCH_2F$ and HF.

9 Claims, No Drawings

(56) References Cited

U.S. PATENT DOCUMENTS

| | | | | |
|---|---|---|---|---|
| 8,058,489 B2* | 11/2011 | Rao | ................... | C07C 17/206 |
| | | | | 570/176 |
| 8,263,816 B2* | 9/2012 | Rao | ................... | C07C 17/00 |
| | | | | 570/156 |
| 10,392,545 B2* | 8/2019 | Rao | ................... | C07C 17/087 |
| 11,053,421 B2* | 7/2021 | Rao | ................... | C07C 17/354 |
| 11,708,516 B2* | 7/2023 | Rao | ................... | C07C 19/08 |
| | | | | 252/67 |
| 11,718,775 B2* | 8/2023 | Peng | ................... | C09K 5/045 |
| | | | | 62/114 |
| 2002/0032356 A1* | 3/2002 | Gelblum | ................... | C07C 17/269 |
| | | | | 422/240 |
| 2004/0089839 A1 | 5/2004 | Thomas et al. | | |
| 2006/0106263 A1 | 5/2006 | Miller et al. | | |
| 2006/0217578 A1 | 9/2006 | Rao et al. | | |
| 2006/0243945 A1 | 11/2006 | Minor et al. | | |
| 2007/0100175 A1 | 5/2007 | Miller et al. | | |
| 2007/0179324 A1 | 8/2007 | Van Der Puy et al. | | |
| 2009/0127496 A1 | 5/2009 | Rao et al. | | |
| 2011/0021849 A1 | 1/2011 | Avril et al. | | |
| 2012/0267567 A1 | 10/2012 | Rao et al. | | |
| 2019/0322917 A1 | 10/2019 | Rao et al. | | |
| 2021/0292627 A1 | 9/2021 | Rao et al. | | |

FOREIGN PATENT DOCUMENTS

| | | |
|---|---|---|
| EP | 0658531 A1 | 6/1995 |
| EP | 0974571 B1 | 4/2003 |
| FR | 2729136 A1 | 7/1996 |
| GB | 938070 A | 9/1963 |
| WO | 9427940 A1 | 12/1994 |
| WO | 2005108334 A1 | 11/2005 |
| WO | 2007019355 A1 | 2/2007 |
| WO | 2007053688 A2 | 5/2007 |
| WO | 2007053689 A2 | 5/2007 |
| WO | 2008002499 A2 | 1/2008 |
| WO | 2008002500 A1 | 1/2008 |
| WO | 2008002501 A2 | 1/2008 |
| WO | 2008040969 A2 | 4/2008 |

OTHER PUBLICATIONS

Schotte, Ind. Eng. Chem. Process Des. Dev, 19, 432-439, 1980.
Walas, Stanley M., Phase Equilibria in Chemical Engineering, 1985, pp. 165 to 244, published by Butterworth Publishers.

* cited by examiner

1,2,3,3,3-PENTAFLUROPROPENE PRODUCTION PROCESSES

FIELD OF THE INVENTION

The present invention relates to processes that involve the production of halogenated hydrocarbon products comprising 1,2,3,3,3-pentafluoropropene.

BACKGROUND OF THE INVENTION

As a result of the Montreal Protocol phasing out ozone depleting chlorofluorocarbons (CFCs) and hydrochlorofluorocarbons (HCFCs), industry has been working for the past few decades to find replacement refrigerants. The solution for most refrigerant producers has been the commercialization of hydrofluorocarbon (HFC) refrigerants. The new hydrofluorocarbon refrigerants, HFC-134a being the most widely used at this time, have zero ozone depletion potential, and thus are not affected by the current regulatory phase out as a result of the Montreal Protocol. The production of other hydrofluorocarbons for use in applications such as solvents, blowing agents, cleaning agents, aerosol propellants, heat transfer media, dielectrics, fire extinguishants and power cycle working fluids has also been the subject of considerable interest.

There is also considerable interest in developing new refrigerants with reduced global warming potential for the mobile air-conditioning market.

HFO-1225ye, having zero ozone depletion and a low global warming potential, has been identified as a potential refrigerant. U.S. Pat. No. 5,396,000 discloses a process for producing HFO-1225ye by dehydrofluorination of $CF_3CFHCF_2H$ (HFC-236ea). There is a need for new manufacturing processes for the production of HFO-1225ye.

SUMMARY OF THE INVENTION

The present invention provides a process for making HFO-1225ye. The process comprises reacting $CF_3CClFCCl_2F$ (CFC-215bb) with $H_2$ in a reaction zone in the presence of a catalyst comprising a catalytically effective amount of palladium supported on a support selected from the group consisting of alumina, fluorided alumina, aluminum fluoride and mixtures thereof, to produce a product mixture comprising HFO-1225ye, wherein the mole ratio of $H_2$ to $CF_3CClFCCl_2F$ fed to the reaction zone is between about 1:1 and about 5:1.

The present invention also provides a composition comprising (a) $CF_3CClFCCl_2F$ and (b) HF; wherein the HF is present in an effective amount to form an azeotropic combination with the $CF_3CClFCCl_2F$.

The present invention also provides a composition comprising (a) 1,1,1,2,3-pentafluoropropane and (b) HF; wherein the HF is present in an effective amount to form an azeotropic combination with the 1,1,1,2,3-pentafluoropropane.

DETAILED DESCRIPTION

The present invention provides a process for making HFO-1225ye from CFC-215bb by reacting CFC-215bb with hydrogen in a reaction zone over a suitable catalyst. HFO-1225ye may exist as one of two configurational isomers, E or Z. HFO-1225ye as used herein refers to the isomers, E-HFO-1225ye (CAS reg no. 5595-10-8) or Z-HFO-1225ye (CAS reg. no. 5528-43-8), as well as any combinations or mixtures of such isomers.

CFC-215bb can be prepared from a variety of starting materials. For example, $CF_3CCl=CCl_2$ can be converted to CFC-215bb as disclosed in U.S. Pat. Nos. 2,466,189 and 2,437,993, which are incorporated herein by reference.

Catalysts suitable for carrying out the process of making HFO-1225ye from CFC-215bb in accordance with this invention comprise palladium and may optionally comprise additional Group VIII metals (e.g., Pt, Ru, Rh or Ni). The palladium is supported on alumina, fluorided alumina, aluminum fluoride or a mixture thereof. The palladium-containing material used to prepare the catalyst is preferably a palladium salt (e.g., palladium chloride). Other metals, when used, may be added to the support during the preparation of the catalyst.

The supported metal catalysts may be prepared by conventional methods known in the art such as by impregnation of the carrier with a soluble salt of the catalytic metal (e.g., palladium chloride or rhodium nitrate) as described by Satterfield on page 95 of *Heterogenous Catalysis in Industrial Practice*, $2^{nd}$ edition (McGraw-Hill, New York, 1991). Palladium supported on alumina is available commercially. Another suitable procedure for preparing a catalyst containing palladium on fluorided alumina is described in U.S. Pat. No. 4,873,381, which is incorporated herein by reference.

By a catalytically effective amount is meant the concentration of catalysts on the support that is sufficient to carry out the catalytic reaction. The concentration of palladium on the support is typically in the range of from about 0.1% to about 10% by weight based on the total weight of the catalyst and is preferably in the range of about 0.1% to about 5% by weight based on the total weight of the catalyst. The concentration of the additional Group VIII metal, when used, is about 3% by weight, or less, based on the total weight of the catalyst; but palladium is ordinarily at least 50% by weight based on the weight of the total metals present on the support, and preferably at least 80% by weight based on the weight of the total metals present on the support.

The relative amount of hydrogen fed during contact of CFC-215bb in a reaction zone containing the palladium-containing catalyst is from about 1 mole of H2 per mole of CFC-215bb to about 5 moles of H2 per mole of CFC-215bb, preferably from about 1 mole of H2 per mole of CFC-215bb to about 4 moles of H2 per mole of CFC-215bb and more preferably from about 1.0 mole of H2 per mole of CFC-215bb to about 3 moles H2 per mole of CFC-215bb.

The reaction zone temperature for the catalytic hydrogenation of CFC-215bb is typically in the range of from about 100° C. to about 400° C., and preferably is in the range of from about 125° C. to about 350° C. The contact time is typically in the range of from about 1 to about 450 seconds, and preferably is in the range of from about 10 to about 120 seconds. The reactions are typically conducted at atmospheric pressure or super atmospheric pressure.

The effluent from the reaction zone typically includes HCl, unreacted hydrogen, HF, HFO1225ye, $CF_3CF=CH_2$ (HFO1234yf) and $CF_3CHFCH_2F$ (HFC-245eb), higher boiling products and intermediates typically including $CF_3CHFCH_2Cl$ (HCFC-244eb), $CF_3CClFCH_2F$ (HCFC-235bb) and $CF_3CF=CFCl$ (HCFO-1215yb) and any unconverted CFC-215bb.

Through proper selection of operating conditions such as temperature, contact time and hydrogen to CFC-215bb ratios, the process of the invention may be operated to produce predominantly mixtures of HCFO-1215yb and HFO-1225ye. The HCFO-1215yb produced by the process of this invention is a useful starting material for the manufacture of the saturated hydrofluorocarbon HFC-245eb.

In accordance with this invention, HF may also be fed in the reaction zone. Of note are embodiments wherein said HF is fed to the reaction zone as an azeotrope or near azeotrope comprising HF and CFC-215bb.

When HF is co-fed along with hydrogen and HCFO-215bb to the reaction zone containing the palladium-containing catalyst at elevated temperature (e.g., about 250° C. or higher), the effluent from the reaction zone normally contains $CF_3CFHCF_2Cl$ (HCFC-226ea) in addition to those compounds present in the product mixture when no HF is present in the feed to the reaction zone (e.g., HCFO-1215yb). Accordingly, this invention provides a process for the preparation of a product mixture comprising HFO-1225ye and HCFC-226ea from CFC-215bb by reacting CFC-215bb with hydrogen in the presence of hydrogen fluoride. Of note are embodiments wherein HCFC-226ea is present in the product mixture; and wherein HCFC-226ea is recovered from the product mixture. The HCFC-226ea can be further processed to produce products containing no chlorine. Of note are embodiments wherein HF is fed to the reaction zone and HFO1225ye, HCFC-226ea and HCFO-1215yb are all present in the product mixture.

When the production of HCFC-226ea is desired, the relative amount of HF fed to the reaction zone is typically from about 1 to 10 moles of HF per mole of hydrogen fed to the reaction zone and is preferably from about 2 to 8 moles of HF per mole of hydrogen fed to the reaction zone.

When the production of HCFC-226ea is desired, the reaction zone temperature for the catalytic hydrogenation of CFC-215bb in the presence of HF is typically in the range of from about 250° C. to about 400° C., and preferably is in the range of from about 300° C. to about 375° C. The contact time is typically in the range of from about 1 to about 450 seconds, and preferably is in the range of from about 10 to about 120 seconds. The reactions are typically conducted at atmospheric pressure or super atmospheric pressure.

When HF is co-fed along with hydrogen and CFC-215bb to the reaction zone containing the palladium-containing catalyst at temperature of less than about 250° C., the effluent from the reaction zone normally contains HFC-245eb in addition to those compounds present in the product mixture when no HF is present in the feed to the reaction zone (e.g., HCFO-1215yb). Accordingly, this invention provides a process for the preparation of a product mixture comprising HFO-1225ye and HFC-245eb from CFC-215bb by reacting CFC-215bb with hydrogen in the presence of hydrogen fluoride. Of note are embodiments wherein HFC-245eb is present in the product mixture; and wherein said HFC-245eb is recovered from the product mixture.

When the production of HFC-245eb is desired, the presence of HF is not critical. If used, the relative amount of HF fed to the reaction zone is typically from about 10 moles of HF per mole of hydrogen fed to the reaction zone or less.

When the production of HFC-245eb is desired, the reaction zone temperature for the catalytic hydrogenation of CFC-215bb in the presence or absence of HF is typically in the range of from about 100° C. to about 250° C., and is preferably in the range of from about 125° C. to about 225° C. The contact time is typically in the range of from about 1 to about 450 seconds, and preferably is in the range of from about 10 to about 120 seconds. The reactions are typically conducted at atmospheric pressure or super atmospheric pressure.

Through proper selection of operating conditions such as temperature, contact time and hydrogen to hydrogen fluoride ratios, the process may be operated to produce a product mixture wherein the halogenated hydrocarbons comprise predominantly of HCFO-1215yb, HCFC-226ea and HFO-1225ye. Alternatively, through proper selection of operating conditions such as temperature, contact time and hydrogen to hydrogen fluoride ratios, the process may be operated to produce a product mixture wherein the halogenated hydrocarbons comprise predominantly of HCFO-1215yb, HFC-245eb and HFO-1225ye.

Of note are embodiments where HFO-1225ye is a desired product and is recovered from the product mixture. The HFO-1225ye present in the effluent from the reaction zone may be separated from the other components of the product mixture and unreacted starting materials by conventional means (e.g., distillation). When HF is present in the effluent, this separation can also include isolation of azeotrope or near azeotrope of HFO-1225ye and HF and further processing to produce HF-free HFC-1225ye by using procedures similar to that disclosed in US Patent Publication US 2006/0106263 A1, which is incorporated herein by reference.

Also of note are embodiments where HFC-1234yf is present in the product mixture and is recovered therefrom. When HFC-1234yf is present in the effluent from the reaction zone, it may also be separated from the other components of the product mixture and unreacted starting materials by conventional means (e.g., distillation). When HF is present in the effluent, this separation can also include isolation of azeotrope or near azeotrope of HFC-1234yf and HF and further processing to produce HF-free HFC-1234yf by using procedures similar to that disclosed in US Patent Publication US 2006/0106263 A1.

Of note are embodiments wherein HFC-245eb is present in the product mixture; and wherein said HFC-245eb is recovered. When HFC-245eb is present in the effluent from the reaction zone, it may also be separated from the other components of the product mixture and unreacted starting materials by conventional means (e.g., distillation). When HF is present in the effluent, this separation can also include isolation of the azeotrope or near azeotrope of HFC-245eb and HF and further processing to produce HF-free HFC-245eb by using procedures similar to those disclosed in US Patent Publication US 2006/0106263 A1. Of note are embodiments wherein HF is fed to the reaction zone and HFC-245eb is present in the product mixture, and wherein at least a portion of HFC-245eb is recovered from the product mixture as an azeotrope comprising HF and HFC-245eb. The HFC-245eb/HF azeotrope can be recycled back to the reactor.

Of note are embodiments wherein HCFO-1215yb is present in the product mixture; and wherein said HCFO-1215yb is recovered. The HCFO-1215yb produced by the processes above can be used as a starting material for the manufacture of the saturated hydrofluorocarbon HFC-245eb by hydrogenation (optionally in the presence of HF). Thus, the present invention also provides a process for making HFC-245eb and HFO-1225ye, comprising: (a) reacting CFC-215bb with hydrogen, optionally in the presence of HF, in a reaction zone in the presence of a catalyst comprising a catalytically effective amount of palladium supported on a support selected from the group consisting of alumina, fluorided alumina, aluminum fluoride and mixtures thereof to produce a product mixture comprising HCFO-1215yb and HFO-1225ye (wherein the mole ratio of H2 to CFC-215bb fed to the reaction zone is between about 1:1 and about 5:1); (b) recovering said HCFO-1215yb; (c) hydrogenating said HCFO-1215yb, optionally in the presence of HF, to HFC-245eb; and (d) recovering HFC-245eb.

The HFO-1225ye produced by the processes above can be used as a starting material for the manufacture of the saturated hydrofluorocarbon HFC-245eb by hydrogenation (optionally in the presence of HF). Thus, the present invention also provides another process for making HFC-245eb, comprising: (a) reacting CFC-215bb with hydrogen, and optionally in the presence of HF, in a reaction zone in the presence of a catalyst comprising a catalytically effective amount of palladium supported on a support selected from the group consisting of alumina, fluorided alumina, aluminum fluoride and mixtures thereof to produce a product mixture comprising HFO-1225ye (wherein the mole ratio of H2 to CFC-215bb fed to the reaction zone is between about 1:1 and about 5:1); (b) recovering said HFO-1225ye; and (c) hydrogenating said HFO-1225ye, optionally in the presence of HF, to HFC 245eb.

The present invention also provides a process for making 1,1,1,2,3,3-hexafluoropropane (HFC-236ea), comprising: (a) reacting CFC-215bb with hydrogen and hydrogen fluoride in a reaction zone in the presence of a catalyst comprising a catalytically effective amount of palladium supported on a support selected from the group consisting of alumina, fluorided alumina, aluminum fluoride and mixtures thereof to produce a product mixture comprising HCFC-226ea in addition to HFO-1225ye (wherein the mole ratio of H2 to CFC-215bb fed to the reaction zone is between about 1:1 and about 5:1); (b) recovering said HCFC-226ea; and (c) hydrogenating said HCFC-226ea to HFC-236ea.

In the above processes for making HFC-245eb or HFC-236ea, the step (a) of the process is conducted under conditions as described above for making HFO-1225ye from CFC-215bb by reacting with hydrogen, optionally in the presence of HF.

In the above processes for making HFC-245eb or HFC-236ea, the step (c) of the process, i.e., the reaction of HCFC-226ea, HCFO-1215yb or HFO-1225ye with hydrogen, optionally in the presence of HF, is carried out in the presence of a hydrogenation catalyst. Hydrogenation catalysts suitable for use in this invention include catalysts comprising at least one metal selected from the group consisting of rhenium, iron, ruthenium, osmium, cobalt, rhodium, iridium, nickel, palladium, and platinum. Said catalytic metal component is typically supported on a carrier such as carbon or graphite or a metal oxide, fluorinated metal oxide, or metal fluoride where the carrier metal is selected from the group consisting of magnesium, aluminum, titanium, vanadium, chromium, iron, and lanthanum. Of note are palladium catalysts supported on carbon (see e.g., U.S. Pat. No. 5,523,501, the teachings of which are incorporated herein by reference).

Also of note are carbon-supported catalysts in which the carbon support has been washed with acid and has an ash content below about 0.1% by weight. Hydrogenation catalysts supported on low ash carbon are described in U.S. Pat. No. 5,136,113, the teachings of which are incorporated herein by reference. Also of note are catalysts comprising at least one metal selected from the group consisting of palladium, platinum, and rhodium supported on alumina ($Al_2O_3$), fluorinated alumina, or aluminum fluoride ($AlF_3$) and mixtures thereof.

The relative amount of hydrogen contacted with HCFC-226ea, HCFO-1215yb or HFO-1225ye, optionally in the presence of HF, when a hydrogenation catalyst is used is typically from about the stoichiometric ratio of hydrogen to the fluorinated organic starting materials to about 10 moles of H2 per mole of the fluorinated organic starting materials. Suitable reaction temperatures are typically from about 100° C. to about 350° C., preferably from about 125° C. to about 300° C. The contact time is typically from about 1 to about 450 seconds, preferably from about 10 to about 120 seconds. The reactions are typically conducted at atmospheric pressure or super atmospheric pressure.

The reactor, distillation columns, and their associated feed lines, effluent lines, and associated units used in applying the processes of this invention should be constructed of materials resistant to hydrogen fluoride and hydrogen chloride. Typical materials of construction, well-known to the fluorination art, include stainless steels, in particular of the austenitic type, the well-known high nickel alloys, such as Monel™ nickel-copper alloys, Hastelloy™ nickel-based alloys and, Inconel™ nickel-chromium alloys, and copper-clad steel.

The present invention also provides azeotrope or near azeotrope compositions comprising an effective amount of hydrogen fluoride combined with a compound selected from CFC-215bb and HFC-245eb.

In connection with developing processes for the separation of the individual compounds from the reaction zone effluent from the reaction of CFC-215bb with hydrogen or with hydrogen and hydrogen fluoride, it is noted that CFC-215bb and HFC-245eb (as well as HFO-1225ye and HFO-1234yf) each can be present as their respective azeotrope or near azeotrope with HF. HF can come from the products of dehydrofluorination reactions of HFC-245eb or intermediates containing five fluorines to compounds containing at least one less fluorine or from HF co-fed along with hydrogen to the reaction zone.

By effective amount is meant an amount, which, when combined with HFC-245eb or CFC-215bb, results in the formation of their respective azeotrope or near azeotrope mixture. As recognized in the art, an azeotrope or a near azeotrope composition is an admixture of two or more different components which, when in liquid form under a given pressure, will boil at a substantially constant temperature, which temperature may be higher or lower than the boiling temperatures of the individual components, and which will provide a vapor composition essentially identical to the liquid composition undergoing boiling.

For the purpose of this discussion, near azeotrope composition (also commonly referred to as an "azeotrope-like composition") means a composition that behaves like an azeotrope (i.e., has constant boiling characteristics or a tendency not to fractionate upon boiling or evaporation). Thus, the composition of the vapor formed during boiling or evaporation is the same as or substantially the same as the original liquid composition. Hence, during boiling or evaporation, the liquid composition, if it changes at all, changes only to a minimal or negligible extent. This is to be contrasted with non-near azeotrope compositions in which during boiling or evaporation, the liquid composition changes to a substantial degree.

Additionally, near azeotrope compositions exhibit dew point pressure and bubble point pressure with virtually no pressure differential. That is to say that the difference in the dew point pressure and bubble point pressure at a given temperature will be a small value. In this invention, compositions with a difference in dew point pressure and bubble point pressure of less than or equal to 3 percent (based upon the bubble point pressure) are considered to be near azeotropes.

Accordingly, the essential features of an azeotrope or a near azeotrope composition are that at a given pressure, the boiling point of the liquid composition is fixed and that the composition of the vapor above the boiling composition is essentially that of the boiling liquid composition (i.e., no fractionation of the components of the liquid composition takes place). It is also recognized in the art that both the boiling point and the weight percentages of each component of the azeotrope composition may change when the azeotrope or near azeotrope liquid composition is subjected to boiling at different pressures. Thus, an azeotrope or a near azeotrope composition may be defined in terms of the unique relationship that exists among the components or in terms of the compositional ranges of the components or in terms of exact weight percentages of each component of the composition characterized by a fixed boiling point at a specified pressure. It is also recognized in the art that various azeotrope compositions (including their boiling points at particular pressures) may be calculated (see, e.g., W. Schotte Ind. Eng. Chem. Process Des. Dev. (1980) 19, 432-439). Experimental identification of azeotrope compositions involving the same components may be used to confirm the accuracy of such calculations and/or to modify the calculations at the same or other temperatures and pressures.

In accordance with this invention, compositions are provided which comprise CFC-215bb and HF wherein HF is present in an effective amount to form an azeotropic combination with the CFC-215bb. These include compositions comprising from about 98.2 mole percent to about 78.0 mole percent HF and from about 1.8 mole percent to about 22.0 mole percent CFC-215bb (which form azeotropes boiling at a temperature from between about −20° C. and about 140° C. and at a pressure from between about 3.05 psi (21.0 kPa) and about 951 psi (6557 kPa)).

Additionally, near azeotrope compositions containing HF and CFC-215bb may also be formed. Such near azeotrope compositions exist around azeotrope compositions. For example, a composition comprising 98.2 mole percent HF and 1.8 mole percent CFC-215bb is an azeotrope composition at −20° C. at 3.05 psi (21.0 kPa). Compositions comprising from about 99.0 mole percent to about 98.15 mole percent HF and from about 1.0 mole percent to about 1.85 mole percent CFC-215bb are near azeotrope compositions. Similarly, at 80° C. and 112.2 psi (773.6 kPa), a composition comprising 91.1 mole percent HF and 8.9 mole percent CFC-215bb is an azeotrope composition, and compositions comprising from about 90.6 mole percent to about 92.4 mole percent HF and from about 9.4 mole percent to about 7.6 mole percent CFC-215bb are near azeotrope compositions. Also, at 140° C. and 951 psi (6557 kPa), a composition comprising 78.0 mole percent HF and 22.0 mole percent CFC-215bb is an azeotrope composition, and compositions comprising from about 77.2 mole percent to about 78.4 mole percent HF and from about 22.8 mole percent to about 21.6 mole percent CFC-215bb are near azeotrope compositions.

Compositions may be formed that consist essentially of azeotrope combinations of hydrogen fluoride with CFC-215bb. These include compositions consisting essentially of from about 98.2 mole percent to about 78.0 mole percent HF and from about 1.8 mole percent to about 22.0 mole percent CFC-215bb (which forms an azeotrope boiling at a temperature from between about −20° C. and about 140° C. and at a pressure from between about 3.05 psi (21.0 kPa) and about 951 psi (6557 kPa)).

At atmospheric pressure, the boiling points of hydrogen fluoride and CFC-215bb are about 19.5° C. and −20° C., respectively. The ratio of relative volatility at 16.76 psi (111.5 kPa) and 20.0° C. of HF to CFC-215bb was found to be nearly 1.0 as 96.2 mole percent HF and 3.8 mole percent CFC-215bb was approached. The ratio of relative volatility at 84.81 psi (585.1 kPa) and 70.0° C. was found to be nearly 1.0 as 92.1 mole percent HF and 7.9 mole percent CFC-215bb was approached. These data indicate that the use of conventional distillation procedures will not result in the separation of a substantially pure compound because of the low difference of relative volatility of the compounds.

To determine the relative volatility of HF with CFC-215bb, the so-called PTx Method was used. In this procedure, the total absolute pressure in a cell of known volume is measured at a constant temperature for various known binary compositions. Use of the PTx Method is described in greater detail in "Phase Equilibrium in Process Design," Wiley-Interscience Publisher, 1970, written by Harold R. Null, on pages 124 to 126, the entire disclosure of which is hereby incorporated by reference. Samples of the vapor and liquid, or vapor and each of the two liquid phases under those conditions where two liquid phases exist, were obtained and analyzed to verify their respective compositions.

These measurements can be reduced to equilibrium vapor and liquid compositions in the cell by an activity coefficient equation model, such as the Non-Random, Two-Liquid (NRTL) equation, to represent liquid phase non-idealities. Use of an activity coefficient equation, such as the NRTL equation, is described in greater detail in "The Properties of Gases and Liquids," 4th Edition, publisher McGraw Hill, written by Reid, Prausnitz and Poling, on pages 241 to 387; and in "Phase Equilibria in Chemical Engineering", published by Butterworth Publishers, 1985, written by Stanley M. Walas, pages 165 to 244; the entire disclosure of each of the previously identified references are hereby incorporated by reference.

Without wishing to be bound by any theory or explanation, it is believed that the NRTL equation can sufficiently predict whether or not mixtures of HF and CFC-215bb behave in an ideal manner and can sufficiently predict the relative volatilities of the components in such mixtures. Thus, while HF has a good relative volatility compared to CFC-215bb at high CFC-215bb concentrations, the relative volatility becomes nearly 1.0 as 3.8 mole percent CFC-215bb was approached at 20.0° C. This would make it impossible to separate CFC-215bb from HF by conventional distillation from such a mixture. Where the ratio of relative volatility approaches 1.0 defines the system as forming a near-azeotrope. Where the ratio of relative volatility is 1.0 defines the system as forming an azeotrope.

It has been found that azeotropes of CFC-215bb and HF are formed at a variety of temperatures and pressures. Azeotrope compositions may be formed between 21.0 kPa (at a temperature of −20° C.) and 6557 kPa (at a temperature of 140° C.) when said compositions consisting essentially of CFC-215bb and HF range from about 98.2 mole percent HF (and 1.8 mole percent CFC-215bb) to about 78.0 mole percent HF (and 22.0 mole percent CFC-215bb). An azeotrope of HF and CFC-215bb has been found at 20.0° C. and 16.76 psi (111.5 kPa) consisting essentially of about 96.2 mole percent HF and about 3.8 mole percent CFC-215bb. An azeotrope of HF and CFC-215bb has also been found at 70.0° C. and 84.81 psi (585.1 kPa) consisting essentially of about 92.1 mole percent HF and about 7.9 mole percent CFC-215bb. Based upon the above findings, azeotrope compositions at other temperatures and pressures may be calculated. It has been calculated that an azeotrope composition of about 98.2 mole percent HF and about 1.8 mole percent CFC-215bb can be formed at −20° C. and 3.05 psi (21.0 kPa) and an azeotrope composition of about 78.0 mole percent HF and about 22.0 mole percent CFC-215bb can be formed at 140° C. and 951 psi (6557 kPa). Accordingly, the present invention provides azeotrope compositions consisting essentially of from about 98.2 mole percent to about 78.0 mole percent HF and from about 1.8 mole percent to about 22.0 mole percent CFC-215bb, said composition having a boiling point of about −20° C. at about 3.05 psi (21.0 kPa) to about 140° C. at about 951 psi (6557 kPa).

The HF/CFC-215bb azeotrope and near azeotrope compositions in the effluent from the reaction zone can be recycled back to the reaction zone and are useful in processes to produce HFC-245eb and HFO-1225ye and in processes to produce HCFC-226ea.

In accordance with this invention, compositions are provided which comprise HFC-245eb and HF wherein HF is present in an effective amount to form an azeotropic combination with the HFC-245eb. According to calculations, these include compositions comprising from about 81.0 mole percent to about 55.0 mole percent HF and from about 19.0 mole percent to about 45.0 mole percent HFC-245eb (which form azeotropes boiling at a temperature of from about −20° C. to about 135° C. and at a pressure of from about 4 psi (27.5 kPa) to about 550 psi (3792 kPa)).

The following specific Examples are to be construed as merely illustrative, and do not constrain the remainder of the disclosure in any way whatsoever.

EXAMPLES

General Procedure for the Preparation of
Palladium on Fluorided Alumina Catalyst A weighed quantity of the catalyst was placed in a ⅝-inch (1.58 cm) diameter Inconel™ nickel alloy reactor tube heated in a fluidized sand bath. The tube was heated from 50° C. to 175° C. in a flow of nitrogen (50 cc/min; $8.3 \times 10^{-7}$ m$^3$/sec) over the course of about one hour. HF was then admitted to the reactor at a flow rate of 50 cc/min ($8.3 \times 10^{-7}$ m$^3$/sec). After 0.5 to 2 hours the nitrogen flow was decreased to 20 cc/min ($3.3 \times 10^{-7}$ m$^3$/sec) and the HF flow increased to 80 cc/min ($1.3 \times 10^{-6}$ m$^3$/sec); this flow was maintained for about 1 hour. The reactor temperature was then gradually increased to 400° C. over 3 to 5 hours. At the end of this period, the HF flow was stopped, and the reactor cooled to the desired operating temperature under 20 sccm ($3.3 \times 10^{-7}$ m$^3$/sec) nitrogen flow. The fluorided alumina was discharged from the reactor for further use or kept in the reactor for catalyst evaluation.

General Procedure for Product Analysis

The following general procedure is illustrative of the method used for analyzing the products of fluorination reactions. Part of the total reactor effluent was sampled on-line for organic product analysis using a gas chromatograph equipped a mass selective detector (GC/MS). The gas chromatography utilized a 20 ft. (6.1 m) long×⅛ in. (0.32 cm) diameter tube containing Krytox® perfluorinated polyether on an inert carbon support. The helium flow was 30 mL/min ($5.0 \times 10^{-7}$ m$^3$/sec). Gas chromatographic conditions were 60° C. for an initial hold period of three minutes followed by temperature programming to 200° C. at a rate of 6° C./minute.

Legend

| | |
|---|---|
| 1234yf is CF$_3$CF═CH$_2$ | 1243zf is CF$_3$CH═CH$_2$ |
| 263fb is CF$_3$CH$_2$CH$_3$ | 245eb is CF$_3$CHFCH$_2$F |
| 235bb is CF$_3$CFClCH$_2$F | 226ea is CF$_3$CHFCF$_2$Cl |
| 244eb is CF$_3$CFHCH$_3$ | 215bb is CF$_3$CFClCFCl$_2$ |
| 1225ye is E and Z forms of CF$_3$CF═CHF | |
| 1215yb is E and Z forms of CF$_3$CF═CFCl | |

Example 1

Reaction of H$_2$ and HF with CFC-215bb Over Palladium on Fluorided Alumina Catalyst A 10.0 g (15 ml) sample of 1% palladium on fluorided alumina catalyst (⅛" extrudates) prepared according to the General Procedure described above for preparation of the catalyst, was placed in a ⅝-inch (1.58 cm) diameter Inconel™ nickel alloy reactor tube heated in a fluidized sand bath. The CFC-215bb was fed from a pump to a vaporizer maintained at about 100-110° C. The vapor was combined with the appropriate molar ratios of HF and hydrogen in a 0.5" (1.27 cm) diameter Monel™ nickel alloy tube packed with Monel™ turnings. The mixture of reactants then entered the reaction zone containing the catalyst. The reactions were conducted at a nominal pressure of one atmosphere. Product analysis was performed as described in the General Procedure for product analysis. The results of the reaction of hydrogen and hydrogen fluoride with CF$_3$CFClCFCl$_2$ over this catalyst at various temperatures are shown in Table 1. Small amounts of other products, not included in Table 1 were also present. The product analytical data is given in units of GC area %. The contact time was 30 seconds except for the last three runs indicated in Table 1.

TABLE 1

| T ° C. | Mol. Ratio H2/215bb/HF | 1234yf | 1243zf | 263fb | Z-1225ye | E-1225ye | 245eb | Z or E-1215yb | E or Z-1215yb | 226ea | 215bb |
|---|---|---|---|---|---|---|---|---|---|---|---|
| 225 | 2/1/4 | 2.6 | ND | 1.6 | 16.7 | 18.0 | 29.3 | 5.6 | 4.3 | ND | 13.2 |
| 250 | 2/1/4 | 3.2 | ND | 1.8 | 21.4 | 20.9 | 20.5 | 8.5 | 6.6 | ND | 9.3 |
| 275 | 2/1/4 | 3.1 | 2.5 | 2.1 | 44.6 | 10.5 | 14.8 | 5.9 | 4.5 | ND | 2.7 |
| 300 | 2/1/4 | 3.1 | 2.8 | 1.9 | 43.8 | 10.7 | 2.5 | 10.4 | 4.7 | ND | 2.3 |
| 300 | 4/1/8 | 16.3 | 0.1 | 7.9 | 28.8 | 7.3 | 24.7 | ND | ND | ND | ND |
| 300 | 1/1/8 | 0.7 | 1.2 | ND | 16.0 | 4.4 | ND | 19.0 | 9.1 | 9.3 | 33.7 |
| 350 | 1/1/8 | 0.7 | 1.2 | ND | 9.6 | 1.4 | ND | 13.8 | 6.1 | 21.3 | 29.4 |
| 350 | 2/1/8 | 3.6 | 1.4 | ND | 28.5 | 8.8 | ND | 15.3 | 7.1 | 17.0 | 3.8 |

ND = not detected

Example 2

Reaction of H2 with CFC-215bb Over Palladium on Alumina Catalyst

A Hastelloy tube (0.625" OD×0.576 ID×10"L) was filled with 15 cc (9.7 g) of commercial 1% palladium on alumina spheres (4 mm). The packed portion of the reactor was heated by a 5.7"×1" ceramic band heater clamped to the outside of the reactor. A thermocouple, positioned between the reactor wall and the heater, measured the reactor temperature. The catalyst was activated by heating at 250° C. for 2 hours with 50 sccm ($8.33 \times 10^{-7}$ m$^3$/s) of nitrogen. The nitrogen was turned off and the catalyst was treated with 50 sccm ($8.33 \times 10^{-7}$ m$^3$/s) of hydrogen at 250° C. for two hours. The reactor was then cooled to the desired operating temperature under a flow of nitrogen. A flow of hydrogen and CFC-215bb was then started through the reactor after stopping the nitrogen flow. The hydrogen to CFC-215bb mole ratio was 2/1 and the contact time was 30 seconds. The products were analyzed by GC/MS and are reported in Table 2 as mole %. Minor amounts of other compounds, not listed in Table 2 were also present.

TABLE 2

| T °C. | 1234yf | Z-1225ye | E-1225ye | 245eb | 235bb | Z or E-1215yb | E or Z-1215yb | 244eb | 215bb |
|---|---|---|---|---|---|---|---|---|---|
| 175 | 7.0 | 25.6 | 24.1 | 8.9 | 7.4 | 5.2 | 3.8 | 14.1 | 1.0 |
| 250 | 4.3 | 33.4 | 14.7 | 1.4 | 2.0 | 16.7 | 8.7 | 6.4 | 0.4 |

Comparative Example

Reaction of H2 with CFC-215bb Over Palladium on Carbon Catalyst

Example 1 was substantially repeated except that the catalyst was commercial 0.5% palladium on carbon (5.4 g, 15.0 ml) and only hydrogen and CFC-215bb were fed to the reactor. The hydrogen to CFC-215bb mole ratio was 2/1 and the contact time was 30 seconds. The GC/MS analytical results of the products, in area %, for various operating temperatures are summarized in Table 3. Minor amounts of other compounds, not listed in Table 3 were also present.

TABLE 3

| T °C. | 263fb | 254eb | 245eb | 235bb |
|---|---|---|---|---|
| 150 | 0.1 | 9.4 | 83.2 | 7.0 |
| 175 | 0.2 | 8.5 | 82.3 | 5.8 |
| 225 | 0.6 | 10.7 | 87.2 | 0.1 |

What is claimed is:

1. A composition comprising HFO-1225ye, CFO-1215yb, and CFO-1234yf, and optionally one or more of HFO-1243zf, HFC-245eb, HCFC-244eb, HCFC-226ea, HCFC-235bb and HFC-263fb.

2. The composition of claim 1 wherein the member comprises HCFC-226ea.

3. The composition of claim 1 wherein the member comprises HFC-245eb.

4. The composition of any of claim 1, 2 or 3, wherein the HFO-1225ye comprises E-HFO-1225ye and Z-HFO-1225ye.

5. The composition of claim 4 wherein the E-HFO-1225ye is present in an amount greater than Z-HFO-1225ye.

6. The composition of claim 4 wherein the E-HFO-1225ye is present in an amount less than Z-HFO-1225ye.

7. A composition comprising Z-HFO-1225ye, CFO-1215yb, and HFO-1234yf, and optionally one or more of E-HFO-1225ye, HFC-263fb, HFO-1243zf, HFC-254eb, HCFC-226ea and HCFC-235bb.

8. A process comprising distilling the composition of any of claims 1-3 and isolating HFO-1225ye.

9. A process comprising distilling the composition of claim 4 and isolating E-HFO-1225ye and Z-HFO-1225ye.

* * * * *